United States Patent [19]
Regel et al.

[11] Patent Number: 4,507,141
[45] Date of Patent: Mar. 26, 1985

[54] TRIAZOLYLALKYL-THIOETHER PLANT GROWTH REGULATORS AND FUNGICIDES

[75] Inventors: Erik Regel, Wuppertal; Karl H. Büchel, Burscheid; Klaus Lürssen, Bergisch-Gladbach; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 354,122

[22] Filed: Mar. 2, 1982

[30] Foreign Application Priority Data

Mar. 7, 1981 [DE] Fed. Rep. of Germany ....... 3108770

[51] Int. Cl.³ .................... A01N 43/64; C07D 249/08
[52] U.S. Cl. ........................................ 71/76; 71/74; 71/78; 71/92; 548/101; 548/262; 514/383; 514/184
[58] Field of Search ................ 548/101, 262; 424/245, 424/269; 71/74, 76, 78, 92

[56] References Cited

U.S. PATENT DOCUMENTS

| | | | |
|---|---|---|---|
| 4,217,129 | 8/1980 | Shephard et al. | 548/341 |
| 4,316,932 | 2/1982 | Kranz et al. | 424/269 |

FOREIGN PATENT DOCUMENTS

| | | | |
|---|---|---|---|
| 112 | 12/1978 | European Pat. Off. | 424/269 |
| 7707 | 2/1980 | European Pat. Off. | 424/269 |
| 22531 | 7/1980 | European Pat. Off. | 424/269 |
| 2645496 | 4/1978 | Fed. Rep. of Germany | 424/269 |

*Primary Examiner*—Alton D. Rollins
*Attorney, Agent, or Firm*—Sprung, Horn, Kramer & Woods

[57] ABSTRACT

Triazolylalkyl-thioether plant growth regulators and fungicides of the formula

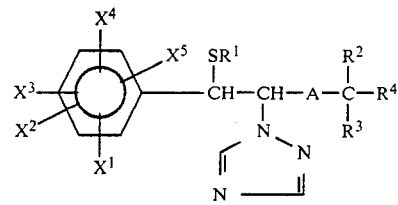

in which
A represents the keto group or the CH(OH) group,
$R^1$ represents alkyl, alkenyl, alkynyl, optionally substituted cycloalkyl, alkylaminoalkyl, alkoxycarbonylalkyl, optionally substituted phenyl or optionally substituted phenylalkyl,
$R^2$ represents alkyl,
$R^3$ represents alkyl or halogenoalkyl,
$R^4$ represents alkyl, halogenoalkyl, alkoxy, alkoxymethyl, alkylthio, alkylthiomethyl, optionally substituted phenyl, optionally substituted benzyl, optionally substituted phenoxy, optionally substituted phenoxymethyl, optionally substituted phenylthio, optionally substituted phenylthiomethyl, alkenyl, alkoxycarbonyl or cyano, or
$R^3$ and $R^4$, conjointly with the carbon atom to which they are bonded, represent optionally substituted cycloalkyl and
$X^1$, $X^2$, $X^3$, $X^4$ and $X^5$ are selected independently and each represent hydrogen, hologen, alkyl, halogenoalkyl, halogenoalkoxy, alkoxy, alkylthio, halogenoalkylthio, alkylamino, dialkylamino, nitro, cyano, hydroxyl, alkoxycarbonyl, optionally substituted phenyl, optionally substituted phenoxy or optionally substituted benzyloxy, or an acid addition salt or metal salt complex thereof.

11 Claims, No Drawings

TRIAZOLYLALKYL-THIOETHER PLANT GROWTH REGULATORS AND FUNGICIDES

The present invention relates to certain new triazolylalkyl-thioethers, to a process for their preparation and to their use as plant growth regulators and fungicides.

It has already been disclosed that 4,4-dimethyl-1-phenyl-triazol-2-yl-pent-1-en-3-ones and -ols exhibit a good fungicidal activity (see Japanese Patent Application J 53/150 661 and DE-OS (German Published Specification) 2,838,847). The fungicidal action of these compounds is however not always fully satisfactory, especially if small amounts and low concentrations are used. The plant growth-regulating action of these azole derivatives is also not always adequate.

Further, it has already been disclosed that 3-cyclopropyl-1-phenyl-triazol-2-yl-prop-1-en-3-ols have good fungicidal and plant growth-regulating properties (see DE-OS (German Published Specification) 3,010,560). The action of these azole derivatives however also leaves something to be desired in certain cases, especially if small amounts and low concentrations are used.

The present invention now provides, as new compounds, the triazolylalkyl-thioethers of the general formula

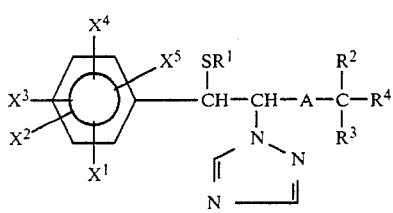

in which
A represents the keto group or the CH(OH) group,
$R^1$ represents alkyl, alkenyl, alkynyl, optionally substituted cycloalkyl, alkylaminoalkyl, alkoxycarbonylalkyl, optionally substituted phenyl or optionally substituted phenylalkyl,
$R^2$ represents alkyl,
$R^3$ represents alkyl or halogenoalkyl,
$R^4$ represents alkyl, halogenoalkyl, alkoxy, alkoxymethyl, alkylthio, alkylthiomethyl, optionally substituted phenyl, optionally substituted benzyl, optionally substituted phenoxy, optionally substituted phenoxymethyl, optionally substituted phenylthio, optionally substituted phenylthiomethyl, alkenyl, alkoxycarbonyl or cyano, or
$R^3$ and $R^4$, conjointly with the carbon atom to which they are bonded, represent optionally substituted cycloalkyl and
$X^1$, $X^2$, $X^3$, $X^4$ and $X^5$ are selected independently and each represent hydrogen, halogen, alkyl, halogenoalkyl, halogenoalkoxy, alkoxy, alkylthio, halogenoalkylthio, alkylamino, dialkylamino, nitro, cyano, hydroxyl, alkoxycarbonyl, optionally substituted phenyl, optionally substituted phenoxy or optionally substituted benzyloxy,
as well as their acid-addition salts and metal-salt complexes.

The compounds of the formula (I) possess two asymmetric carbon atoms; they can therefore exist in the erythro-form as well as in the threo-form. In both cases they are predominantly in the form of racemates.

The invention also provides a process for the preparation of a triazolylalkyl-thioether of the formula (I), or an acid addition salt or metal salt complex thereof, in which
(a) a vinyltriazolyl derivative of the general formula

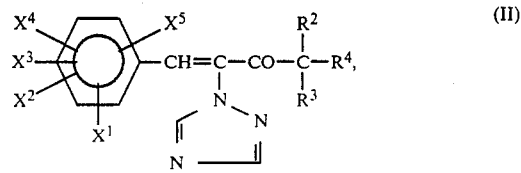

in which $R^2$, $R^3$, $R^4$, $X^1$, $X^2$, $X^3$, $X^4$ and $X^5$ have the abovementioned meanings,
is reacted with a mercaptan of the general formula

in which $R^1$ has the abovementioned meaning,
in the presence of a diluent and, if appropriate, in the presence of a base, or
(b) a vinyltriazole derivative of the general formula

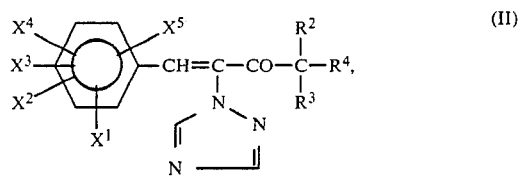

in which $R^2$, $R^3$, $R^4$, $X^1$, $X^2$, $X^3$, $X^4$ and $X^5$ have the abovementioned meanings,
is reacted with a salt of an isothiourea of the general formula

in which
$R^1$ has the abovementioned meaning and
Z represents an inorganic acid,
in the presence of a diluent and in the presence of a base, or
(c) a triazolylalkyl-thioether-keto derivative, obtainable according to process variant (a) or (b), of the general formula

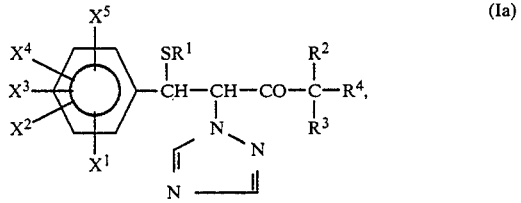

in which $R^1$, $R^2$, $R^3$, $R^4$, $X^1$, $X^2$, $X^3$, $X^4$ and $X^5$ have the abovementioned meanings,
is reduced and
(d) thereafter, if desired, the compound of the formula (I) obtained in variant (a), (b) or (c) is subjected to an addition reaction with an acid or a metal salt.

It has been found that the novel triazolylalkyl-thioethers of the formula (I) and their physiologically acceptable acid addition salts and metal salt complexes exhibit powerful plant growth-regulating properties and powerful fungicidal properties.

Surprisingly, the compounds of the formula (I), their acid addition salts and metal salt complexes exhibit a better plant growth-regulating action and fungicidal action than the 4,4-dimethyl-1-phenyl-triazol-2-yl-pent-1-en-3-ones and -ols, and the 3-cyclopropyl-1-phenyl-triazol-2-yl-prop-1-en-3-ols, known from the prior art, which are related compounds both chemically and in respect of their action. The active compounds according to the invention thus represent an enrichment of the art.

The formula (I) provides a general definition of the triazolylalkyl-thioethers according to the invention. Preferred compounds are those in which $R^1$ represents straight-chain or branched alkyl with 1 to 4 carbon atoms, alkenyl or alkynyl with in either case 2 to 4 carbon atoms, cycloalkyl with 3 to 7 carbon atoms which is optionally substituted by alkyl with 1 to 4 carbon atoms, alkylaminoalkyl or alkoxycarbonylalkyl with in either case 1 to 4 carbon atoms in each alkyl part, or optionally substituted phenyl or optionally substituted phenylalkyl with 1 to 4 carbon atoms in the alkyl part, possible substituents in either case being the radicals mentioned below as preferred meanings for $X^1$, with the exception of hydrogen;

$R^2$ represents straight-chain or branched alkyl with 1 to 4 carbon atoms;

$R^3$ represents straight-chain or branched alkyl with 1 to 4 carbon atoms or halogenoalkyl with 1 to 4 carbon atoms and 1 to 5 identical or different halogen atoms (especially fluorine, chlorine and bromine atoms);

$R^4$ represents straight-chain or branched alkyl with 1 to 4 carbon atoms, halogenoalkyl with 1 to 4 carbon atoms and 1 to 5 identical or different halogen atoms (especially fluorine, chlorine and bromine atoms), alkoxy, alkoxymethyl, alkylthio or alkylthiomethyl, each with 1 to 4 carbon atoms in the alkyl part, or an optionally substituted phenyl, benzyl, phenoxy, phenoxymethyl, phenylthio or phenylthiomethyl group, possible substituents in each case being the radicals mentioned below as preferred meanings for $X^1$, with the exception of hydrogen, or $R^4$ represents alkenyl with 2 to 4 carbon atoms, alkoxycarbonyl with 1 to 4 carbon atoms in the alkoxy part, or cyano; or $R^3$ and $R^4$, conjointly with the carbon atom to which they are bonded, represent optionally substituted cycloalkyl with 3 to 7 carbon atoms, possible substituents being halogen, alkyl with 1 to 4 carbon atoms or halogenoalkenyl with 2 to 4 carbon atoms and up to 5 identical or different halogen atoms (especially fluorine and chlorine atoms);

$X^1$ represents hydrogen, fluorine, chlorine, bromine, straight-chain or branched alkyl, alkoxy or alkylthio, each with 1 to 4 carbon atoms, halogenoalkyl, halogenoalkoxy or halogenoalkylthio, each with 1 or 2 carbon atoms and up to 5 identical or different halogen atoms (especially fluorine atoms and chlorine atoms), alkylamino or dialkylamino with in either case 1 or 2 carbon atoms in each alkyl part, nitro, cyano, hydroxyl, alkoxycarbonyl with 1 to 4 carbon atoms in the alkoxy part or an optionally substituted phenyl, phenoxy or benzyloxy group, preferred substituents being fluorine, chlorine, bromine and alkyl with 1 or 2 carbon atoms;

$X^2$ represents hydrogen, fluorine, chlorine, bromine, straight-chain or branched alkyl, alkoxy or alkylthio, each with 1 to 4 carbon atoms, halogenoalkyl, halogenoalkoxy or halogenoalkylthio, each with 1 or 2 carbon atoms and up to 5 identical or different halogen atoms (especially fluorine atoms and chlorine atoms), alkylamino or dialkylamino with in either case 1 or 2 carbon atoms in each alkyl part, nitro, cyano, hydroxyl, alkoxycarbonyl with 1 to 4 carbon atoms in the alkoxy part or an optionally substituted phenyl, phenoxy or benzyloxy group, preferred substituents being fluorine, chlorine, bromine and alkyl with 1 or 2 carbon atoms;

$X^3$ represents hydrogen, fluorine, chlorine, bromine, straight-chain or branched alkyl, alkoxy or alkylthio, each with 1 to 4 carbon atoms, halogenoalkyl, halogenoalkoxy or halogenoalkylthio, each with 1 or 2 carbon atoms and up to 5 identical or different halogen atoms (especially fluorine atoms and chlorine atoms), alkylamino or dialkylamino with in either case 1 or 2 carbon atoms in each alkyl part, nitro, cyano, hydroxyl, alkoxycarbonyl with 1 to 4 carbon atoms in the alkoxy part or an optionally substituted phenyl, phenoxy or benzyloxy group, preferred substituents being fluorine, chlorine, bromine and alkyl with 1 or 2 carbon atoms; and $X^4$ and $X^5$ each represent hydrogen. Particularly preferred compounds of the formula (I) are those in which $R^1$ represents straight-chain or branched alkyl with 1 to 4 carbon atoms, allyl, vinyl, but-2-enyl, propargyl, optionally methyl-substituted or ethyl-substituted cyclohexyl, methylaminomethyl, ethylaminomethyl, methoxycarbonylmethyl, ethoxycarbonylmethyl, or optionally substituted phenyl or benzyl, possible substituents in either case being the radicals mentioned below as particularly preferred meanings for $X^1$, with the exception of hydrogen;

$R^2$ represents methyl or ethyl;

$R^3$ represents optionally fluorine-, chlorine- or bromine-substituted methyl;

$R^4$ represents optionally fluorine-, chlorine- or bromine-substituted methyl, alkoxy, alkoxymethyl, alkylthio or alkylthiomethyl, each with 1 or 2 carbon atoms in the alkyl part, or optionally substituted phenyl, benzyl, phenoxy, phenoxymethyl, phenylthio or phenylthiomethyl, possible substituents in each case being the radicals mentioned below as particularly preferred meanings for $X^1$, with the exception of hydrogen, or $R^4$ represents vinyl, allyl, methoxycarbonyl, ethoxycarbonyl or cyano; or $R^3$ and $R^4$, conjointly with the carbon atom to which they are bonded, represent optionally chlorine- or methyl-substituted cyclopropyl;

$X^1$ represents hydrogen, fluorine, chlorine, straight-chain or branched alkyl with 1 to 4 carbon atoms, methoxy, methylthio, isopropoxy, trifluoromethyl, difluorochloromethyl, trifluoromethoxy, trifluoromethylthio, dimethylamino, nitro, cyano, hydroxyl, acetoxy, tert.-butylcarbonyloxy or an optionally fluorine-, chlorine- or methyl-substituted phenyl, phenoxy or benzyloxy group;

$X^2$ represents hydrogen, fluorine, chlorine, straight-chain or branched alkyl with 1 to 4 carbon atoms, methoxy, methylthio, isopropoxy, trifluoromethyl, difluorochloromethyl, trifluoromethoxy, trifluoromethylthio, dimethylamino, nitro, cyano, hydroxyl, acetoxy, tert.-butylcarbonyloxy or an optionally fluorine-, chlorine- or methyl-substituted phenyl, phenoxy or benzyloxy group;

$X^3$ represents hydrogen, fluorine, chlorine, straight-chain or branched alkyl with 1 to 4 carbon atoms, methoxy, methylthio, isopropoxy, trifluoromethyl, difluorochloromethyl, trifluoromethoxy, trifluoromethylthio, dimethylamino, nitro, cyano, hydroxyl, acetoxy, tert.-butylcarbonyloxy or an optionally fluorine-, chlorine- or methyl-substituted phenyl, phenoxy or benzyloxy group; and $X^4$ and $X^5$ represent hydrogen. Furthermore, acid addition salts of compounds of the formula (I), in which A represents the keto group or the CH(OH) group and $R^1$, $R^2$, $R^3$, $R^4$, $X^1$, $X^2$, $X^3$, $X^4$ and $X^5$ have the preferentially mentioned meanings, are also preferred. Particularly preferred, amongst these, are acid addition salts which result from addition of a hydrogen halide acid (for example hydrobromic acid or, especially, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) or sulphonic acids (for example p-toluenesulphonic acid and 1,5-naphthalenedisulphonic acid).

Metal salt complexes of compounds of the formula (I) in which

A represents the keto group or the CH(OH) group and $R^1$, $R^2$, $R^3$, $R^4$, $X^1$, $X^2$, $X^3$, $X^4$ and $X^5$ have the preferentially mentioned meanings, are also preferred. Particularly preferred amongst these are metal salt complexes which contain, as cations, metals of main groups II to IV or of sub-groups I and II or IV to VIII of the periodic table of the elements, examples to be mentioned being copper, zinc, manganese, magnesium, tin, iron and nickel.

Anions of these metal salt complexes are preferably those which are derived from hydrogen halide acids (especially hydrochloric acid and hydrobromic acid), phosphoric acid, nitric acid and sulphuric acid.

If for example, 4,4-dimethyl-1-(4-fluorophenyl)-2-(1,2,4-triazol-1-yl)-pent-1-en-3-one and thiophenol are used as starting materials in process variant (a), the course of the reaction can be represented by the following equation:

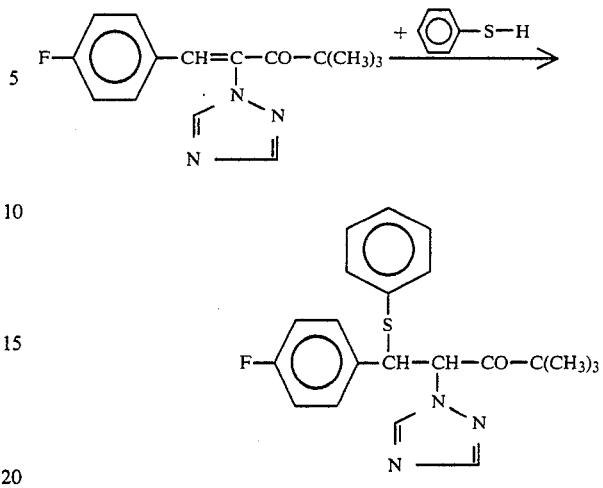

If, for example, 1-(4-chlorophenyl)-4,4-dimethyl-2-(1,2,4-triazol-1-yl)-pent-1-en-3-one and S-methyl-isothiourea sulphate are used as starting materials in process variant (b), the course of the reaction can be represented by the following equation:

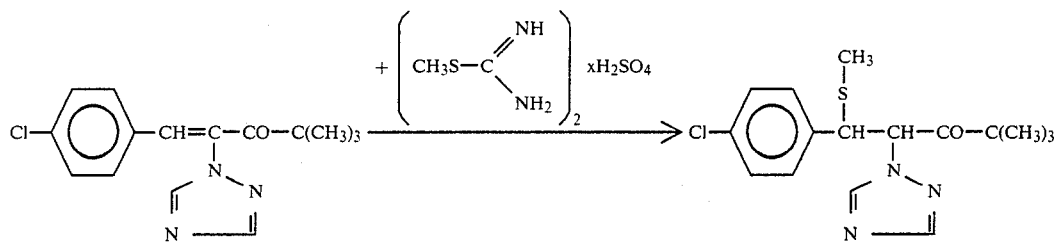

If, for example, 1-(4-chlorophenyl)-4,4-dimethyl-1-methylthio-2-(1,2,4-triazol-1-yl)-pentan-3-one and sodium borohydride are used as starting materials in process variant (c), the course of the reaction can be represented by the following equation:

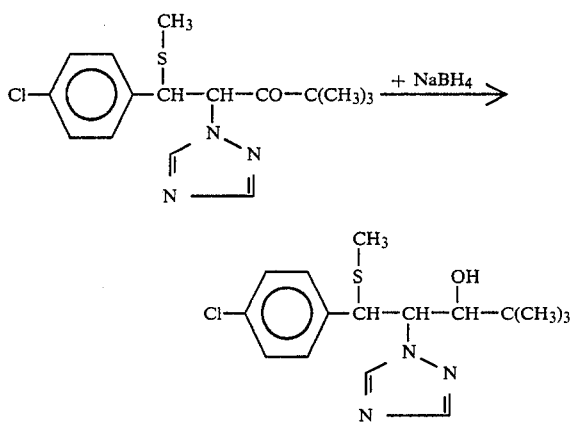

The formula (II) provides a general definition of the vinyltriazole derivatives required as starting materials in carrying out process variants (a) and (b). In this formula $R^2$, $R^3$, $R^4$, $X^1$, $X^2$, $X^3$, $X^4$ and $X^5$ preferably have those meanings which have already been mentioned preferentially for these radicals in connection with the description of the compounds of the formula (I).

Some of the vinyltriazolyl derivatives of the formula (II) are known (see Japanese Patent Application 53/130,661; German Patent Application 2,838,847, German Patent Application 3,010,560, U.S. application Ser. No. 223,066 filed Jan. 7, 1981, now abandoned); some of them are the subject of U.S. application Nos. 276,842 filed June 24, 1981, now abandoned, 283,307 filed July 14, 1981, now abandoned, and 320,043 filed Nov. 10, 1981, now abandoned. They can be obtained in accordance with the processes mentioned there, for example by reacting corresponding ketones with the corresponding benzaldehydes in the usual manner in the presence of an inert organic solvent, for example toluene, and in the presence of a catalyst, for example piperidine acetate, at temperatures between 20° and 160° C., especially at the boiling point of the particular solvent.

The vinyltriazole derivatives of the formula (I) exist as the geometrical isomers E(trans) and Z(cis). In the E,Z nomenclature, the substituents present on the double bond are classified in decreasing priority according to the Cahn-Ingold-Prelog rule. If the preferred substituents are present on the same side of the double bond, the configuration is called Z (derived from the German word "zusammen", i.e. "together"), whereas if they are on the opposite side, the configuration is called E (derived from the German word "entgegen", i.e. "opposite").

An unambiguous characterizing feature of the two geometrical isomers is the $H^1$ nuclear resonance of the two triazole protons. The difference in the shift values of these two protons is about twice as great in the E-forms as in the corresponding Z-forms.

The vinyltriazole derivatives of the formula (II) can be employed either as the E,Z isomer mixture or in the form of the individual E and Z isomers.

The formula (III) provides a general definition of the mercaptans also required as starting materials for process variant (a). In this formula, $R^1$ preferably represents those radicals which have already been mentioned preferentially for these substituents in connection with the description of the compounds of the formula (I).

The mercaptans of the formula (III) are generally known compounds of organic chemistry.

The formula (IV) provides a general definition of the salts of isothioureas additionally required as starting materials for process variant (b). In this formula, $R^1$ preferably represents those radicals which have already been mentioned preferentially for these substituents in connection with the description of the compounds of the formula (I). Z preferably represents an inorganic oxyacid, for example sulphuric acid, phosphoric acid or nitric acid, or a hydrogen halide acid, for example hydrochloric acid or hydrobromic acid.

The isothioureas of the formula (IV) are generally known compounds of organic chemistry.

The triazolylalkyl-thioether-keto derivatives of the formula (Ia) required as starting materials for process variant (c) are themselves compounds according to the invention.

Preferred diluents for process variant (a) are inert organic solvents. These include, as preferences, ketones, such as acetone and methyl ethyl ketone; alcohols, such as methanol, ethanol and isopropanol; nitriles, such as acetonitrile and propionitrile; aromatic hydrocarbons, such as benzene, toluene or xylene; and ethers, such as diethyl ether or tetrahydrofuran.

Process variant (a) is carried out in the presence of a base, if appropriate. Preferred bases are alkali metal alcoholates, for example sodium methylate or ethylate or potassium methylate or ethylate; alkali metal amides, for example sodium amide or potassium amide; and alkali metal hydrides, for example sodium hydride.

In process variant (a), the reaction temperatures can be varied within a substantial range. In general, the reaction is carried out at between 0° and 120° C., preferably at from 20° to 80° C.

In carrying out process variant (a), preferably 1 to 2 mols of mercaptan of the formula (III) are employed per mol of vinyltriazole derivative of the formula (II), if appropriate together with a catalytic to equimolar amount of base. The end products of the formula (I) may be isolated in a generally customary and known manner.

Preferred diluents for process variant (b) are inert organic solvents. These include, as preferences, the solvents already mentioned as preferred in connection with process variant (a).

Process variant (b) is carried out in the presence of a base. Any customarily usable inorganic or organic base can be added, such as an alkali metal carbonate, for example sodium carbonate, potassium carbonate or sodium bicarbonate, a lower tertiary alkylamine, cycloalkylamine or aralkylamine, such as triethylamine, dimethylbenzylamine or cyclohexylamine, or an alkali metal alcoholate, such as sodium methylate or sodium ethylate.

The reaction temperatures in process variant (b) can be varied within a substantial range. In general, the reaction is carried out at between 20° and 150° C., preferably at the boiling point of the solvent.

In carrying out process variant (b), preferably the equivalent amount of isothiourea of the formula (IV), and 1 to 4 mols of base, are employed per mol of vinyltriazole derivative of the formula (II). The end products of the formula (I) may be isolated in a generally customary and known manner.

The reduction in accordance with process variant (c) may be carried out in a customary manner, for example by reaction with a complex hydride, if appropriate in the presence of a diluent, or by reaction with aluminum isopropylate in the presence of a diluent.

If a complex hydride is used, possible diluents for the reaction in process variant (c) are polar organic solvents. These include, as preferences, alcohols, such as methanol, ethanol, butanol and isopropanol, and ethers, such as diethyl ether or tetrahydrofuran. The reaction is in general carried out at from −10° to +30° C., preferably at from −10° to 20° C. For this reaction, about 1 mol of a complex hydride, such as sodium borohydride, calcium borohydride or lithium alanate, is generally employed per mol of the ketone of the formula (Ia). The compounds according to the invention may be isolated in a customary manner.

If aluminum isopropylate is used, preferred diluents for the reaction in process variant (c) are alcohols, such as isopropanol, or inert hydrocarbons, such as benzene. Reaction temperatures can here also be varied within a substantial range; in general, the reaction is carried out at between 20° and 120° C., preferably at from 50° to 100° C. To carry out the reaction, about 1 to 2 mols of aluminum isopropylate are generally employed per mol of the corresponding ketone of the formula (Ia). The compounds according to the invention may be isolated in a customary manner.

Preferred acids for the preparation of the acid addition salts of the compounds of the formula (I) are those which have already been mentioned as preferred acids in connection with the description of the acid addition salts according to the invention.

The acid addition salts of the compounds of the formula (I) can be obtained in a simple manner according to customary methods of forming salts, for example by dissolving a compound of the formula (I) in a suitable inert solvent and adding the acid, for example hydrochloric acid, and can be isolated in a known manner, for example by filtering off, and be purified, if desired, by washing with an inert organic solvent.

Preferred salts for the preparation of metal salt complexes of compounds of the formula (I) are salts of those anions and cations which have already been mentioned as preferred in connection with the description of the metal salt complexes according to the invention.

The metal salt complexes of compounds of the formula (I) can be obtained in a simple manner according to customary processes, for example by dissolving the metal salt in an alcohol, for example ethanol, and adding the solution to the compound of the formula (I). Metal salt complexes can be isolated in a known manner, for example by filtering off, and can be purified, if desired, by recrystallization.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and athletic fields, at borders, at airports or in fruit orchards. The inhibition of growth of herbaceous and woody plants at borders and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or large fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content of soya or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usally unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits tratement of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, such as, for example, against the powdery mildew of barley or cereal causative organism (*Erysiphe graminis*); and for combating rice diseases, such as, for example, *Pellicularia sasakii*.

It should be emphasized that the active compounds according to the invention not only display a protective action, but also have a systemic action. It is thus possible to protect plants from fungal attack if the active compounds are fed to the above-ground parts of the plant via the soil and the root or via the seed.

When applied in appropriate amounts, the compounds according to the invention also exhibit herbicidal actions.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming or coating. Furthermore, it is possible to apply the active compounds in accordance with the ultra-low volume (ULV) process or to inject the active compound preparation or the active compound itself into the soil. It is also possible to treat the seeds of the plants.

When the compounds according to the invention are used as plant growth regulators, the amounts applied can be varied within a substantial range. In general, 0.01 to 50 kg, preferably 0.05 to 10 kg, are employed per hectare of soil surface.

When the substances according to the invention are used as fungicides, the amount applied can also be varied within a substantial range, depending on the type of application. Especially in the treatment of parts of plants, the active compound concentrations in the use forms are, in general, between 1 and 0.0001% by weight, preferably between 0.5 and 0.001% by weight. In the treatment of seed, amounts of active compound of in general 0.001 to 50 kg per kilogram of seed, preferably 0.01 to 10 g, are required. For the treatment of soil, active compound concentrations of in general 0.00001 to 0.1% by weight, preferably 0.0001 to 0.2%, are required at the place of action.

The present invention also provides a fungicidal or plant growth regulating composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual method of providing a harvested crop may be improved by the present invention.

The examples which follow show the preparation of the compounds according to the invention.

PREPARATIVE EXAMPLES

Example 1

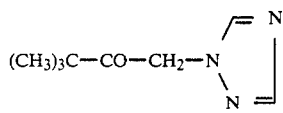
(a)

138 g (2 mol) of 1,2,4-triazole were added in portions, at room temperature, to 276.4 g (2 mol) of ground potassium carbonate and 269.2 g (2 mol) of α-chloropinacoline in 500 ml of acetone, in the course of which the internal temperature rose to the boil. The reaction mixture was stirred for 5 hours under reflux and was then cooled to room temperature and filtered, and the filtrate was concentrated by distilling off the solvent in vacuo. The oily residue crystallized after addition of benzene. 240.8 g (72% of theory) of 3,3-dimethyl-1-(1,2,4-triazol-1-yl)-butan-2-one, of melting point 62°-64° C., were obtained.

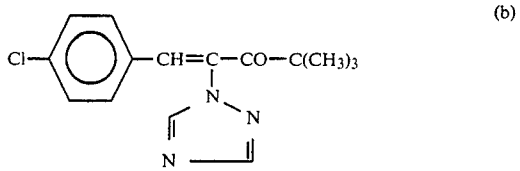
(b)

167 g (1 mol) of 3,3-dimethyl-1-(1,2,4-triazol-1-yl)-butan-2-one and 140.5 g (1 mol) of 4-chlorobenzaldehyde were dissolved in 700 ml of toluene and 1.2 g (0.02 mol) of glacial acetic acid and 1.8 ml (0.02 mol) of piperidine were added. The reaction mixture was heated for 40 hours to 120° C., while continuously separating off the water of reaction. Thereafter the reaction mixture was concentrated in vacuo and the oil which remained was distilled (boiling range 130°-160° C./0.04 mm Hg). The distillate was stirred with ethanol, whereupon crystals separated out. These were filtered off and dried. 35 g (12% of theory) of 1-(4-chlorophenyl)-4,4-dimethyl-2-(1,2,4-triazol-1-yl)-pent-1-en-3-one (E isomer) of melting point 110° C. were thus obtained.

The ethanol mother liquor was concentrated and the oil which remained was dissolved in diisopropyl ether, which caused crystallization to occur. After recrystallization from diisopropyl ether, 25.5 g (8.8% of theory) of 1-(4-chlorophenyl)-4,4-dimethyl-2-(1,2,4-triazol-1-yl)-pent-1-en-3-one (Z isomer), of melting point 82° C., were obtained.

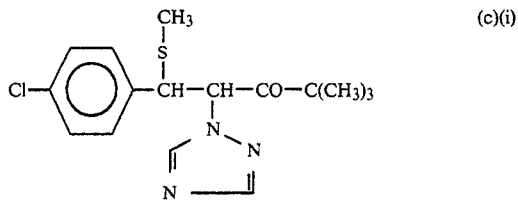
(c)(i)

Process variant (a):

10 g (0.2 mol) of methylmercaptan were introduced into a solution of 0.5 g (9 millimol) of sodium methylate in 300 ml of ethanol. 47 g (0.16 mol) of 1-(4-chlorophenyl)-4,4-dimethyl-2-(1,2,4-triazol-1-yl)-pent-1-en-3-one (E isomer) were introduced into this solution. The initially clear solution soon changed to a thick crystal slurry. The crystals were filtered off, washed with diisopropyl ether and with ethanol, and dried. 36 g (66.6% of theory) of 1-(4-chlorophenyl)-4,4-dimethyl-1-methylthio-2-(1,2,4-triazol-1-yl)-pentan-3-one of melting point 145° C. were obtained.

(ii)

Process variant (b)

289 g (1 mol) of 1-(4-chlorophenyl)-4,4-dimethyl-2-(1,2,4-triazol-1-yl)-pent-1-en-3-one (E,Z isomer mixture) and 139 g (0.5 mol) of S-methylisothiourea sulphate were suspended in 2.5 liters of ethanol and 336 g (4 mol) of sodium bicarbonate were added in portions, while stirring. The mixture was heated under reflux for 4 hours, cooled to room temperature and poured onto water. The organic constituents were extracted with methylene chloride. The organic phase was dried over sodium sulphate, filtered and evaporated down. The resulting oil was caused to crystallize by stirring it with diisopropyl ether, and the crystals were recrystallized from ethanol. 42 g (12% of theory) of 1-(4-chlorophenyl)-4,4-dimethyl-1-methylthio-2-(1,2,4-triazol-1-yl)-pentan-3-one of melting point 145° C. were obtained.

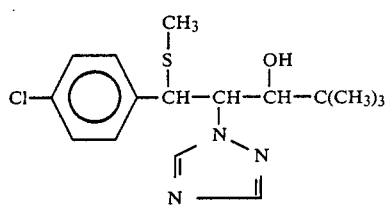 (d)

Process variant (c):

A solution of 2.7 g (0.0703 mol) of sodium boranate in 25 ml of water was added dropwise to a suspension of 33.75 g (0.1 mol) of 1-(4-chlorophenyl)-4,4-dimethyl-1-methylthio-2-(1,2,4-triazol-1-yl)-pentan-3-one and 7.6 g (0.0683 mol) of anhydrous calcium chloride in 200 ml of isopropanol at −5° C. The mixture was then stirred for 15 hours. After having added 20 ml of acetone the mixture was evaporated down in vacuo. The residue was stirred into water and the mixture was repeatedly extracted by shaking with methylene chloride. The methylene chloride phase was dried over sodium sulphate, filtered and evaporated down in vacuo. 32.6 g (96% of theory) of 1-(4-chlorophenyl)-4,4-dimethyl-1-methylthio-2-(1,2,4-triazol-1-yl)-pentan-3-ol, of melting point 58°–60° C., were obtained.

Example 2

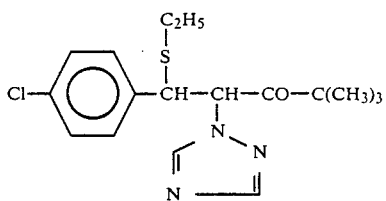

Process variant (a)

28.9 g (0.1 mol) of 1-(4-chlorophenyl)-4,4-dimethyl-2-(1,2,4-triazol-1-yl)-pent-1-en-3-one (E isomer) were introduced into a suspension of 8.4 g (0.1 mol) of sodium ethylmercaptide in 250 ml of ether. The mixture was stirred for 20 hours and was then evaporated down in vacuo. The residue was introduced into water and extracted with methylene chloride. The methylene chloride solution was dried over sodium sulphate, filtered and evaporated down in vacuo. The crystalline residue was stirred with diisopropyl ether and filtered off. 14.9 g (44.9% of theory) of 1-(4-chlorophenyl)-4,4-dimethyl-1-ethylthio-2-(1,2,4-triazol-1-yl)-pentan-3-one, of melting point 154° C., were obtained.

Example 3

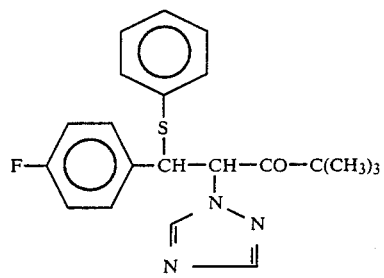

Process variant (a)

27.3 g (0.1 mol) of 4,4-dimethyl-1-(4-fluorophenyl)-2-(1,2,4-triazol-1-yl)-pent-1-en-3-one (E,Z isomer mixture) and 11 g (0.1 mol) of thiophenol were stirred with 100 ml of ethanol at room temperature. After 1 hour, the crystals which had separated out were filtered off and dried. 34.7 g (91% of theory) of 4,4-dimethyl-1-(4-fluorophenyl)-1-phenylthio-2-(1,2,4-triazol-1-yl)-pentan-3-one, of melting point 175° C., were obtained.

Example 4

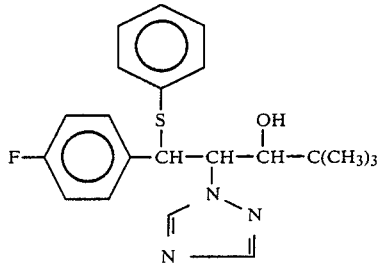

Process variant (c)

9.5 g (25 millimols) of 4,4-dimethyl-1-(4-fluorophenyl)-1-phenylthio-2-(1,2,4-triazol-1-yl)-pentan-3-one (Example 3) were suspended in 150 ml of isopropyl alcohol and 0.5 g (12.5 millimols) of sodium borohydride were added in portions. After 2 days, the mixture was evaporated down in vacuo and the residue was decomposed with dilute acetic acid. The organic phase was taken up in methylene chloride, and the methylene chloride solution was washed with water, dried over sodium sulphate, filtered and evaporated down in vacuo. The crystalline residue was stirred with diisopropyl ether; the crystals were filtered off and dried. 7.5 g (77.9% of theory) of 4,4-dimethyl-1-(4-fluorophenyl)-1-phenylthio-2-(1,2,4-triazol-1-yl)-pentan-3-ol, of melting point 171° C., were obtained.

Example 5

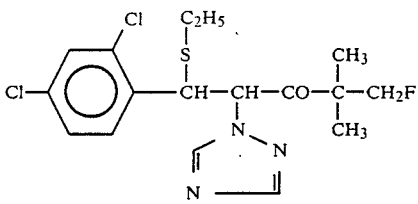

Process variant (a)

4.4 ml (0.059 mol) of ethylmercaptan were added to a suspension of 3.19 g (0.059 mol) of sodium methylate in 200 ml of diethyl ether. After 2 hours, 20.2 g (0.059 mol) of 1-(2,4-dichlorophenyl)-4,4-dimethyl-5-fluoro-2-(1,2,4-triazol-1-yl)-pent-1-en-3-one (E isomer) were introduced. The mixture was stirred for 18 hours at 25° C. and was then evaporated down in vacuo. The residue was introduced into water and the mixture was extracted with methylene chloride. The methylene chloride solution was dried over sodium sulphate, filtered and evaporated down in vacuo. The oil which remained was caused to crystallize by stirring with diisopropyl ether. 13 g (54.6% of theory) of 1-(2,4-dichlorophenyl)-4,4-dimethyl-1-ethylthio-5-fluoro-2-(1,2,4-triazol-1-yl)-pentan-3-one, of melting point 130° C., were obtained.

Example 6

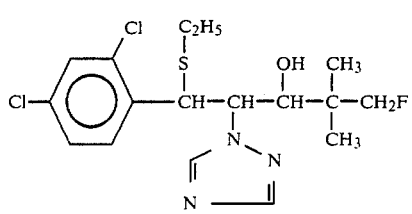

Process variant (c)

A solution of 0.42 g (11 millimols) of sodium boranate in 20 ml of water was added dropwise, with stirring, to a suspension of 6.4 g (15.8 millimols) of 1-(2,4-dichlorophenyl)-4,4-dimethyl-1-ethylthio-5-fluoro-2-(1,2,4-triazol-1-yl)-pentan-3-one (see Example 5) and 1.2 g (10.8 millimols) of calcium chloride in 150 ml of isopropanol. The mixture was stirred for 18 hours at 0° C. and 20 ml of acetone were then added dropwise. This mixture was evaporated in vacuo and the residue was decomposed with dilute acetic acid. The organic base was dissolved in methylene chloride and the solution was washed with water, dried over sodium sulphate, filtered and evaporated down in vacuo. The oil which remained was stirred with diisopropyl ether. 3.9 g (60% of theory) of 1-(2,4-dichlorophenyl)-4,4-dimethyl-1-ethylthio-5-fluoro-2-(1,2,4-triazol-1-yl)-pentan-3-ol, of melting point 182° C., were obtained.

The compounds of the general formula

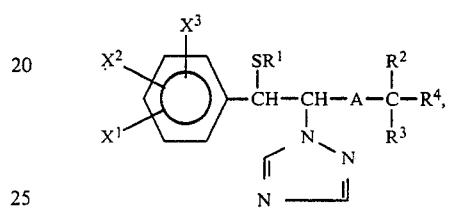

listed in Table 1 which follows were obtained by methods analogous to those in the above examples, and in accordance with the processes mentioned.

TABLE 1

| Compound No. | $X^1$ | $X^2$ | $X^3$ | $R^1$ | | A | $R^2$ | $R^3$ | $R^4$ | Melting point (°C.) |
|---|---|---|---|---|---|---|---|---|---|---|
| 8 | 4-Cl | H | H | phenyl | | CO | $CH_3$ | $CH_3$ | $CH_3$ | 184 |
| 9 | 4-Cl | H | H | 4-Cl-phenyl | | CO | $CH_3$ | $CH_3$ | $CH_3$ | 132 |
| 10 | 4-F | H | H | 4-Cl-phenyl | | CO | $CH_3$ | $CH_3$ | $CH_3$ | 149 |
| 11 | 3-Cl | H | H | 4-Cl-phenyl | | CO | $CH_3$ | $CH_3$ | $CH_3$ | 152 |
| 12 | 4-Cl | H | H | $C_2H_5$ | | CO | $CH_3$ | $CH_3$ | $-CH_2SC_2H_5$ | $n_D^{20}$: 1.5578 |
| 13 | 4-Cl | H | H | 4-Cl-phenyl | | CO | $CH_3$ | $CH_3$ | $-CH_2F$ | 129 |
| 14 | 4-Cl | H | H | 4-Cl-phenyl | | CO | $CH_3$ | $CH_3$ | $-CH_2Cl$ | 146 |
| 15 | 2-Cl | 4-Cl | H | $C_2H_5$ | | CH(OH) | $CH_3$ | $CH_3$ | $CH_3$ | 180 |

TABLE 1-continued

| Compound No. | $X^1$ | $X^2$ | $X^3$ | $R^1$ | | A | $R^2$ | $R^3$ | $R^4$ | Melting point (°C.) |
|---|---|---|---|---|---|---|---|---|---|---|
| 16 | 4-F | H | H | | 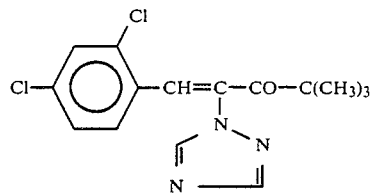 | CH(OH) | $CH_3$ | $CH_3$ | $CH_3$ | 201 |
| 17 | 4-Cl | H | H | $C_4H_9$ | | CO | $CH_3$ | $CH_3$ | $CH_3$ | 80 |
| 18 | 4-Cl | H | H | $C_2H_5$ | | CH(OH) | $CH_3$ | $CH_3$ | $CH_3$ | 170 |
| 19 | 4-F | H | H | $CH_3$ | | CH(OH) | $CH_3$ | $CH_3$ | $-CH_2Cl$ | viscous oil |
| 20 | 4-Cl | H | H | $C_2H_5$ | | CH(OH) | $CH_3$ | $CH_3$ | $-CH_2SC_2H_5$ | 96 |
| 21 | 4-Cl | H | H | $C_4H_9$ | | CH(OH) | $CH_3$ | $CH_3$ | $CH_3$ | 165 |
| 22 | 4-Cl | H | H | | 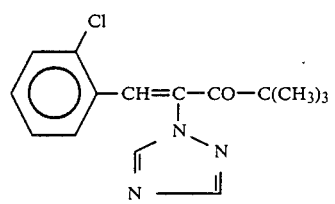 | CH(OH) | $CH_3$ | $CH_3$ | $CH_3$ | 180 |
| 23 | 4-Cl | H | H | | 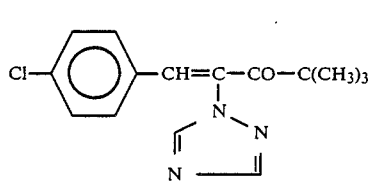 | CH(OH) | $CH_3$ | $CH_3$ | $-CH_2Cl$ | 88 |
| 24 | 3-Cl | H | H | | 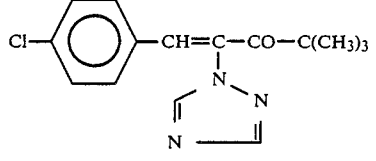 | CH(OH) | $CH_3$ | $CH_3$ | $CH_3$ | 148 |

USE EXAMPLES

The plant growth regulating and fungicidal activity of the compounds of this invention is illustrated by the following biotest examples.

In these examples, the compounds according to the present invention are each identified by the number (given in brackets) from the preparative examples and Table 1.

The known comparison compounds are identified as follows:

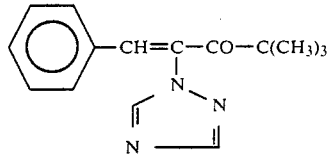
(A)

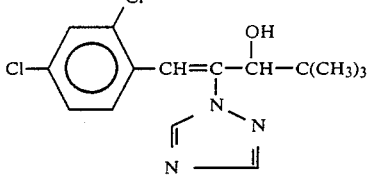
(B)

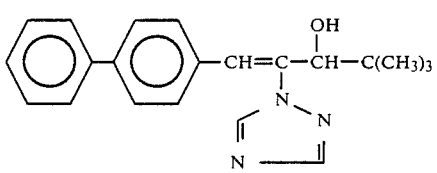
(C)

(D)

(E)

(F)

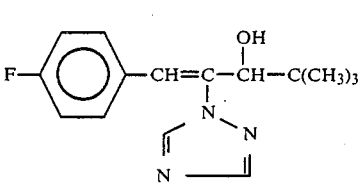
(G)

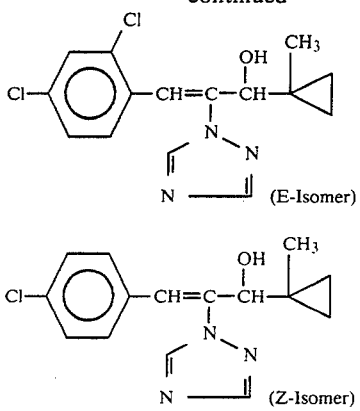

(H) (E-Isomer)

(I) (Z-Isomer)

EXAMPLE 7

Inhibition of growth of grass (*Festuca pratensis*)

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Grass (*Festuca pratensis*) was grown in a greenhouse up to a height in growth of 5 cm. At this stage, the plants were sprayed with the preparations of active compound until dripping wet. After 3 weeks, the additional growth was measured and the inhibition of growth in percent of the additional growth of the control plants was calculated. 100% inhibition of growth meant that growth had stopped and 0% denoted a growth corresponding to that of the control plants.

In this test, active compound (1) exhibited a better inhibition of growth than the compounds (A), (B), (C), (E), (F), (G), (H) and (I) known from the prior art.

EXAMPLE 8

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were grown in a greenhouse to the 2-leaf stage. At this stage, the plants were sprayed with the preparations of active compound until dripping wet. After 3 weeks, the additional growth was measured on all plants and the inhibition of growth in percent of the additional growth of the control plants was calculated. 100% inhibition of growth meant that growth had stopped and 0% denoted a growth corresponding to that of the control plants.

In this test, active compound (1) exhibited a better inhibition of growth than the compounds (A), (B), (C), (G), (H), and (I) known from the prior art.

EXAMPLE 9

Influence on growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. At this stage, the plants were sprayed with the preparations of active compound until dripping wet. After 14 days, the additional growth of the plants was measured and the influence on growth in percent of the additional growth of the control plants was calculated. 0% influence on growth denoted a growth which corresponded to that of the control plants. Negative values characterized an inhibition of growth in comparison to the control plants, whereas positive values characterized a promotion of growth in comparison to the control plants.

In this test, active compounds (1), (2) and (8) exhibited a better influence than the compounds (A), (B), (D) and (F) known from the prior art.

EXAMPLE 10

Inhibition of growth of soybeans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soybean plants were grown in a greenhouse until the first secondary leaf had unfolded completely. At this stage, the plants were sprayed with the preparations of active compound until dripping wet. After 3 weeks, the additional growth wa measured on all the plants and the inhibition of growth in percent of the additional growth of the control plants was calculated. 100% inhibition of growth meant that growth had stopped and 0% denoted a growth corresponding to that of the control plants.

In this test, active compounds (1) and (9) exhibited a better action than the compounds (A), (B), (D), (F), (H) and (I) known from the prior art.

EXAMPLE 11

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. At this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

In this test, active compounds (1), (4) and (10) exhibited a better inhibition of growth than the compounds (A), (B), (D), (E), (F) and (G) known from the prior art.

EXAMPLE 12

Erysiphe test (barley)/protective

Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the compounds (A) and (B) known from the prior art was shown, for example, by the compounds (2), (1), (9), (10), (4) and (16).

EXAMPLE 13

Powdery mildew of barley test (*Erysiphe graminis* var. *hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was shown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had unfolded their first leaf, they were dusted with fresh spores of Erysiphe graminis var. hordei and grown at 21°–22° C. and 80–90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, a clearly superior activity compared with the compounds (A) and (F) known from the prior art was shown, for example, by the compound (1).

It will be appreciated that the instant specification and examples are set forth by way of illustration and not limitation, and that various modifications and changes may be made without departing from the spirit and scope of the present invention.

We claim:

1. A triazolylalkyl-thioether of the formula

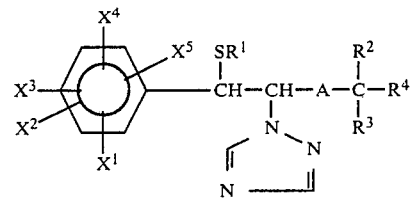

in which

A represents the keto group or the CH(OH) group, $R^1$ represents alkyl with 1 to 4 carbon atoms of phenyl optionally substituted by at least one of fluorine, chlorine, bromine and alkyl with 1 to 4 carbon atoms, $R^2$ represents alkyl with 1 to 4 carbon atoms, $R^3$ represents alkyl with 1 to 4 carbon atoms, $R^4$ represents alkyl with 1 to 4 carbon atoms, halogenoalkyl with 1 to 4 carbon atoms and 1 to 5 halogen atoms, or represents alkylthiomethyl with 1 to 4 carbon atoms in the alkyl moiety, $X^1$ represents hydrogen, fluorine, chlorine or bromine, $X^2$ represents hydrogen, fluorine or chlorine, and $X^3$ represents hydrogen or chlorine, or an acid addition salt or metal salt complex thereof.

2. A compound according to claim 1, in which the addition salt thereof is with an acid selected from hydrogen halide acids, phosphoric acid, nitric acid, sulphuric acid, sulphonic acids and monofunctional or bi-functional carboxylic or hydroxycarboxylic acids, or in the metal salt complex thereof, the metal is with copper, zinc, manganese, magnesium, tin, iron or nickel and the anion is halide, phosphate, nitrate or sulphate.

3. A compound according to claim 1, wherein such compound is 1-(4-chlorophenyl)-4,4-dimethyl-1-methylthio-2-(1,2,4-triazol-1-yl)-pentan-3-ol of the formula

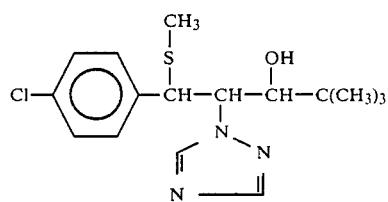

or an acid addition or metal salt complex thereof.

4. A compound according to claim 1, wherein such compound is 4,4-dimethyl-1-(4-fluorophenyl)-1-phenylthio-2-(1,2,4-triazol-1-yl)-pentan-3-ol of the formula

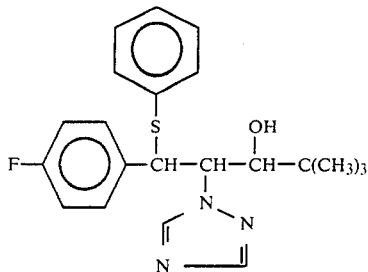

or an acid addition salt or metal salt complex thereof.

5. A compound according to claim 1, wherein such compound is 4,4-dimethyl-1-(4-chlorophenyl)-1-(4-chlorophenylthio)-2-(1,2,4-triazol-1-yl)-pentan-3-one of the formula

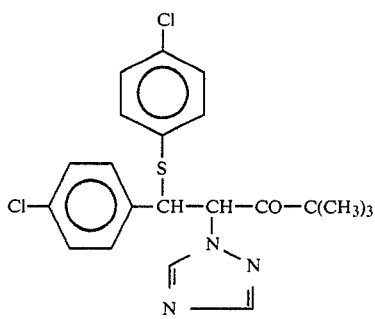

or an acid addition salt or metal salt complex thereof.

6. A compound according to claim 1, wherein such compound is 4,4-dimethyl-1-(4-fluorophenyl)-1-(4-chlorophenylthio)-2-(1,2,4-triaziol-1-yl)-pentan-3-one of the formula

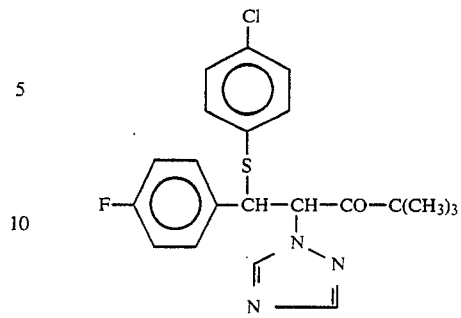

or an acid addition salt or metal salt complex thereof.

7. A compound according to claim 1, wherein such compound is 4,4-dimethyl-1-(4-fluorophenyl)-1-(4-chlorophenylthio)-2-(1,2,4-triazol-1-yl)-pentan-3-ol of the formula

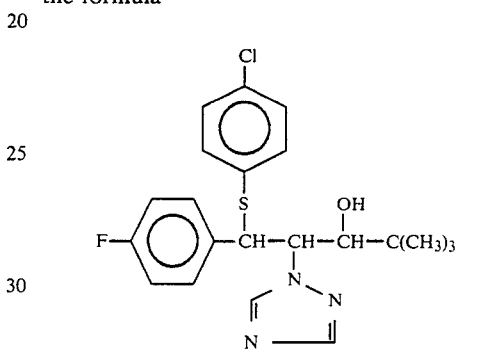

or an acid addition salt or metal salt complex thereof.

8. A fungicidal or plant-growth-regulating composition, comprising a fungicidally or plant-growth-regulating effective amount of a compound, salt or complex according to claim 1 in admixture with a diluent.

9. A method of combating fungi comprising applying to the fungi, or to a habitat thereof, a fungicidally effective amount of a compound, salt or complex according to claim 1.

10. A method of regulating the growth of plants comprising applying to the plants, or to a habitat thereof a plant-growth-regulating effective amount of a compound, salt or complex according to claim 1.

11. The method according to claim 9 or 10 wherein such compound is
1-(4-chlorophenyl)-4,4-dimethyl-1-methylthio-2-(1,2,4-triazol-1-yl)-pentan-3-ol,
4,4-dimethyl-1-(4-fluorophenyl)-1-phenylthio-2-(1,2,4-triazol-1-yl)-pentan-3-ol,
4,4-dimethyl-1-(4-chlorophenyl)-1-(4-chlorophenylthio)-2-(1,2,4-triazol-1-yl)-pentan-3-one
4,4-dimethyl-1-(4-fluorophenyl)-1-(4-chlorophenylthio)-2-(1,2,4-triazol-1-yl)-pentan-3-one, or
4,4-dimethyl-1-(4-fluorophenyl)-1-(4-chlorophenylthio)-2-(1,2,4-triazol-1-yl)-pentan-3-ol,
or an acid addition salt or metal salt complex thereof.

* * * * *

UNITED STATES PATENT AND TRADEMARK OFFICE
CERTIFICATE OF CORRECTION

PATENT NO. : 4,507,141

DATED : March 26, 1985

INVENTOR(S) : Erik Regel, et al

It is certified that error appears in the above-identified patent and that said Letters Patent is hereby corrected as shown below:

| | |
|---|---|
| Col. 14, line 4 | Delete "benzene" and substitute --benzine-- |
| Col. 18, line 8 | After "organic" delete "base" and substitute --phase-- |
| Col. 22, line 43 | Delete "wa" and substitute --was-- |
| Col. 22, line 47 | Delete "shown" and substitute --sown-- |
| Col. 24, line 21 | After "atoms" delete "of" and substitute --or-- |
| Col. 24, line 46 | Delete "with" after "is" |
| Col. 24, line 64 | After "addition" insert --salt-- |
| Col. 25, line 57 | Correct spelling of "triazol" |

Signed and Sealed this

Thirteenth Day of August 1985

[SEAL]

Attest:

DONALD J. QUIGG

Attesting Officer

Acting Commissioner of Patents and Trademarks